United States Patent
Gopalsamy et al.

(10) Patent No.: US 7,285,667 B2
(45) Date of Patent: Oct. 23, 2007

(54) PROCESS FOR THE SYNTHESIS OF FUNCTIONALIZED INDOLIZIDINES

(75) Inventors: Ariamala Gopalsamy, Mahwah, NJ (US); Mengxiao Shi, New Rochelle, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/407,752

(22) Filed: Apr. 20, 2006

(65) Prior Publication Data

US 2006/0241306 A1    Oct. 26, 2006

Related U.S. Application Data

(60) Provisional application No. 60/674,791, filed on Apr. 26, 2005.

(51) Int. Cl.
*C07D 221/24* (2006.01)
(52) U.S. Cl. .................................................. 546/183
(58) Field of Classification Search ................ 546/183
See application file for complete search history.

(56) References Cited

U.S. PATENT DOCUMENTS 5,028,614 A    7/1991    Liu et al.

OTHER PUBLICATIONS

Park et al, 2001, Tetrahedron: Asymmetry, vol. 12, p. 2621-2624.*
Ring Closing Metathesis (RCM), retrieved from Internet on Mar. 16, 2007, <http://www.organic-chemistry.org/namedreactions/ring-closing-metathesis.shtm>.*
Patil et al., "A Short and Efficient Synthesis of 1-deoxy-castanospermine and 1-deoxy-8a-*epi*-castanospermine", Tetrahedron Letters, vol. 42 (2001) pp. 747-749.
Koskinen et al., "Polyhydroxylated Indolizidine Alkaloids-an Efficient Synthesis of 1-deoxy-8,8a-di-*epi*-castanospermine", Tetrahedron, vol. 59 (2003) pp. 6947-6954.

* cited by examiner

*Primary Examiner*—Rebecca Anderson
*Assistant Examiner*—Karen Cheng
(74) *Attorney, Agent, or Firm*—Stephen E. Johnson

(57) ABSTRACT

The present invention provides a process for the preparation of functionalized indolizidines comprising the steps and products disclosed within this application.

6 Claims, No Drawings

PROCESS FOR THE SYNTHESIS OF FUNCTIONALIZED INDOLIZIDINES

This application claims priority from copending provisional application Ser. No. 60/674,791, filed Apr. 26, 2005, the entire disclosure of which is hereby incorporated by reference.

BACKGROUND OF THE INVENTION

Indolizidine alkaloids as a class of heterocycles are well represented in the area of medicinal chemistry, acting on a number of targets including glucosidases, T-cell fusion helper cells, etc. with the potential treatment of HIV, diabetes, cancer, and obesity. Ring closing metathesis ("RCM") a powerful method for carbon-carbon bond formation and the utility of ring closing metathesis has expanded in the recent past and has become a well-recognized synthetic strategy for both carbocycles and heterocycles. Towards our attempt to synthesize a number of analogs with the indolizidine scaffold with various functionalities we were interested in developing a synthetic route that does not rely on a carbohydrate as the starting synthon. The process of this invention provides a synthetic sequence that utilizes the RCM for the construction of functionalized indolizidines from proline.

The following experimental details are set forth to aid in an understanding of the invention, and are not intended, and should not be construed to limit in any way the invention set forth in the claims that follow thereafter.

BRIEF SUMMARY OF THE INVENTION

The invention of this application is a process of making functionalized indolizidines which comprises:
  (a) adding a nitrogen protecting group to proline methyl ester;
  (b) reducing the protected proline methyl ester with a reducing agent in a nonprotic solvent to give an aldehyde;
  (c) adding a vinyl magnesium bromide to the aldehyde of step (b) to obtain an alcohol;
  (d) adding a protecting agent to the alcohol of step (c) in the presence of a base;
  (e) closing the ring in the presence of a catalyst to give a indolizidine scaffold;
  (f) reacting the scaffold in step (e) with an oxidizing agent to yield an epoxide; and
  (g) exposing the compound in step (f) to acidic conditions to yield a functionalized indolizidine.

DETAILED DESCRIPTION OF THE INVENTION

The process of the invention is shown in Scheme I:

Scheme 1

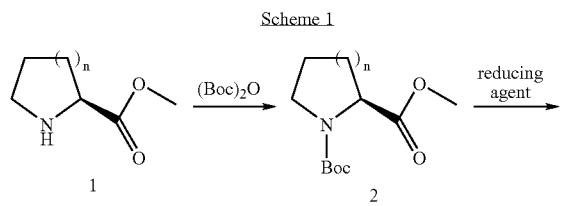

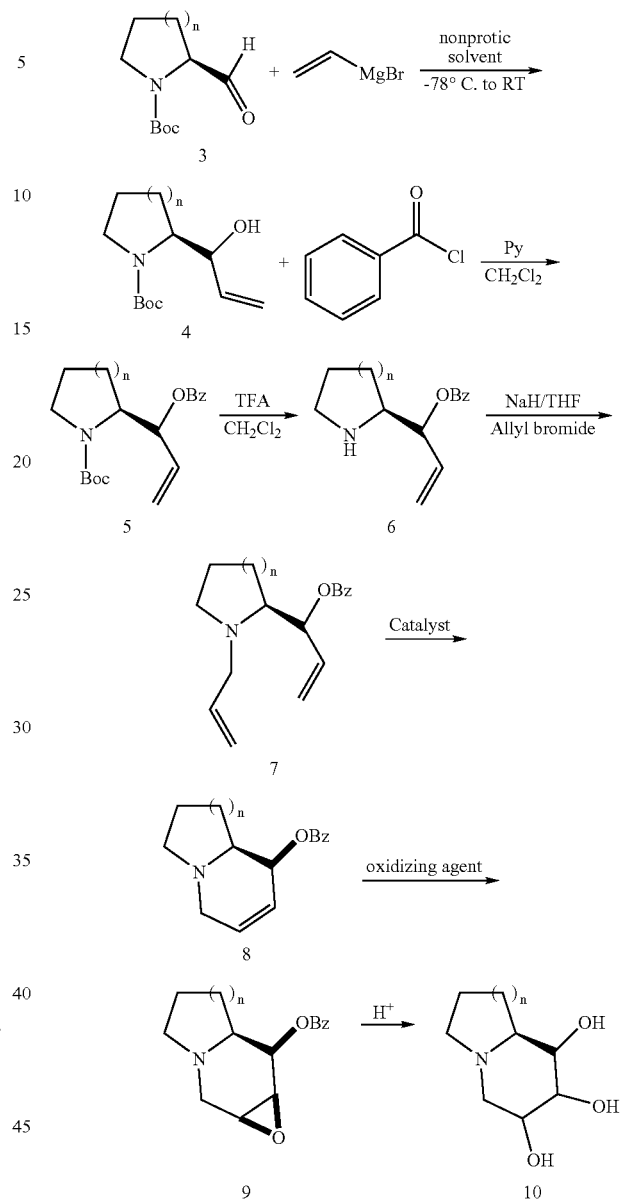

EXAMPLE 1

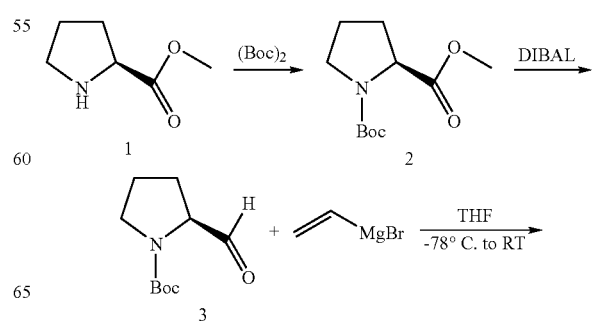

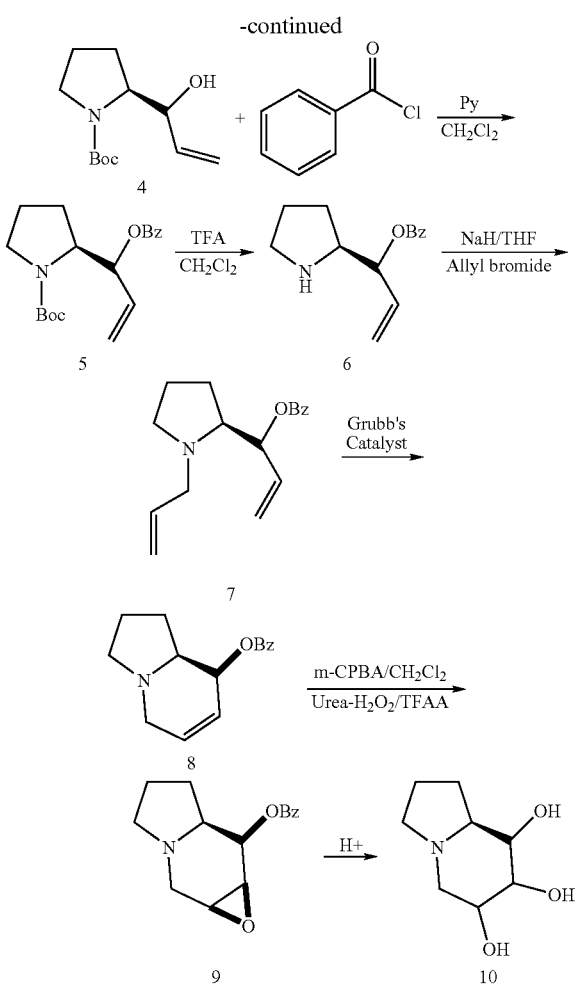

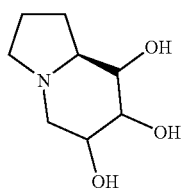

Proline methyl or ethyl ester 1 is protected with a suitable protecting group like tert-butyloxycarbonyl using a reagent like boc anhydride and reduced with a reducing agent like DIBAL in a noprotic solvent like THF to give the aldehyde 3. Addition of vinyl magnesium bromide gives the alcohol 4, which is protected with a suitable protecting group like benzoate 5 by treatment with benzoyl chloride in the presence of a base like pyridine. Deprotection of the amino group of 5 followed by allylation affords the intermediate 7. 7 is subjected to ring closing metathesis with a suitable catalyst like first or second generation Grubb's catalyst or a further modified version of the catalyst to give the indolizidine scaffold 8. Further functionalization of the olefin by treatment with an oxidizing agent like m-CPBA or urea-hydrogen peroxide complex affords the epoxide 9. Opening of the epoxide under acidic condition can afford products like the 6-deoxycastanospermine analogs 10.

For purposes of this invention a base includes alkali metal hydroxides, alkali metal acetates, pyridine, 4-dimethylaminopyridine, sodium carbonate, inorganic carbonates and potassium carbonate.

For purposes of this invention a solvent includes benzene, toluene, acetonitrile, diphenyl ether, or tetrahydrofuran (THF). In a preferred embodiment the solvent is a mixture of biphenyl and diphenyl ether.

What is claimed is:

1. A process of making a functionalized indolizidine of formula which comprises:
(a) adding a nitrogen protecting group to proline methyl ester;
(b) reducing the protected proline methyl ester with a reducing agent in a nonprotic solvent to give an aldehyde;
(c) adding a vinyl magnesium bromide to the aldehyde of step (b) to obtain an alcohol;
(d) adding a nitrogen protecting agent to the alcohol of step (c) in the presence of a base;
(e) deprotecting the nitrogen of step (d) and adding an allyl group, to the nitrogen;
(f) closing the ring in the presence of a catalyst to give an indolizidine scaffold;
(g) reacting the indolizidine scaffold of step (f) with an oxidizing agent to yield an epoxide; and
(h) exposing the epoxide of step (g) to acidic conditions to yield a functionalized indolizidine.

2. The process of claim 1 step (b) wherein the reducing agent is DIBAL.

3. The process of claim 1 step (a) wherein the protecting group is boc anhydride.

4. The process of claim 1 step (b) wherein the solvent is THF.

5. The process of claim 1 step (f) wherein catalyst is Grubb's catalyst.

6. The process of claim 1 step (g) wherein the oxidizing agent is m-CPBA or urea-hydrogen peroxide.

* * * * *